(12) United States Patent
Chavers

(10) Patent No.: US 8,496,605 B1
(45) Date of Patent: Jul. 30, 2013

(54) SPINAL TRACTION DEVICE

(76) Inventor: Bryan Chavers, Fairfield, TX (US)

(*) Notice: Subject to any disclaimer, the term of this patent is extended or adjusted under 35 U.S.C. 154(b) by 246 days.

(21) Appl. No.: 12/977,300

(22) Filed: Dec. 23, 2010

Related U.S. Application Data

(60) Provisional application No. 61/293,645, filed on Jan. 9, 2010.

(51) Int. Cl.
*A61F 5/00* (2006.01)

(52) U.S. Cl.
USPC .............................................. 602/32; 602/35

(58) Field of Classification Search
USPC .... 602/32, 33, 34, 35, 36, 38, 39, 40; 482/10, 482/62, 69; 128/845, 846, 847; 5/621, 622, 5/623, 624, 635, 647; 606/241–242
See application file for complete search history.

(56) References Cited

U.S. PATENT DOCUMENTS

| | | | |
|---|---|---|---|
| 2,633,124 A | 11/1950 | Yellin | |
| 2,808,049 A | 10/1957 | Graham | |
| 3,003,498 A | 12/1958 | Hotas | |
| 3,068,859 A | 12/1962 | Treutelaar | |
| 5,074,287 A | 12/1991 | Avitt | |
| 5,409,452 A * | 4/1995 | Aversano | 602/32 |
| 5,658,245 A | 8/1997 | McGinnis et al. | |

* cited by examiner

*Primary Examiner* — Patricia Bianco
*Assistant Examiner* — Ophelia A Hawthorne
(74) *Attorney, Agent, or Firm* — Kenneth L Tolar

(57) ABSTRACT

A traction device includes a base panel having a frame member pivotally attached to an edge thereof. The frame member is formed of a telescoping leg with a telescoping arm extending from its upper end. The frame member supports a tensioning cable having a neck harness at a distal end for fastening to a patient's head. A proximal end of the cable is attached to a tensioning mechanism slidably mounted on the leg. The tensioning mechanism includes a telescoping, pneumatic cylinder that is extended with a compressible bulb. The cylinder engages a pivotal lever that pulls the cable downwardly when the cylinder is extended, thereby applying tension to the harness.

5 Claims, 2 Drawing Sheets

SPINAL TRACTION DEVICE

CROSS REFERENCE TO RELATED APPLICATIONS

This application is entitled to the benefit of provisional application No. 61/293,645 filed on Jan. 9, 2010, the specification of which is incorporated herein by reference.

BACKGROUND OF THE INVENTION

The present invention relates to a device that allows a patient to easily apply spinal traction in a home or office.

DESCRIPTION OF THE PRIOR ART

Spinal traction is often applied to patients having various back or neck ailments. Conventional in-home devices are difficult to erect and often require the assistance of another person. Furthermore, because the devices are typically mounted on a door, the user is prevented from performing other tasks, such as watching television. Accordingly, there is currently a need for an easier, more convenient means of applying traction.

A review of the prior art reveals a myriad of traction devices. For example, U.S. Pat. No. 2,808,049 issued to Graham discloses a traction device including a vertical support having a plate at a lower end for anchoring beneath a chair; at an upper end is an arm that supports a spring-biased head harness for applying traction to a user's spine.

U.S. Pat. No. 5,074,287 issued to Avitt discloses a cervical traction device including a pivoting arm having a head harness at one end and a weight stack on an opposing end. A motorized cam intermittently raises the weight stack to periodically relieve the applied traction.

U.S. Pat. No. 3,003,498 issued to Hotas discloses a spinal traction chair including a frame having a seat supported thereon. A desired amount of weight may be loaded onto a traction device to apply a desired amount of traction force to a harness.

U.S. Pat. No. 2,633,124 issued to Yellin discloses a traction apparatus including a seat having a post vertically extending therefrom. A harness at the upper end of the post is variably tensioned by a motor beneath the seat.

U.S. Pat. No. 5,658,245 issued to McGinnis et al. discloses a traction device that is attachable to a vehicle seat.

U.S. Pat. No. 3,068,859 issued to Treutelaar discloses a therapeutic traction device comprising a base frame having a shaft vertically extending therefrom; a spring-biased tensioning cord and associated head harness are secured to an upper end of the shaft.

As indicated above, at least one of the references, the patent to Graham, discloses a traction device that can be supported by a chair. However, all of the prior art devices use springs, weight stacks or motors to apply tension to a traction cable. Such mechanisms are bulky, heavy, expensive and require numerous components, which are difficult to construct, assemble and operate. Furthermore, none of the prior art devices include a means for adjusting the traction vector to assure that it is parallel to a chair backrest. The present invention addresses this need by providing a traction device having an expandable, pneumatic cylinder that applies a desired amount of tension to a traction cable; a head harness is mounted on a pivotal frame that can be angularly adjusted to be parallel to a chair backrest, regardless of its slope.

SUMMARY OF THE INVENTION

The present invention relates to a traction device comprising a base panel having a frame member pivotally attached to an edge thereof. The frame member is formed of a telescoping leg with a telescoping arm extending from its upper end. The frame member supports a tensioning cable having a neck harness at a distal end for fastening to a patient's head. A proximal end of the cable is attached to a tensioning mechanism slidably mounted on the leg. The tensioning mechanism includes a telescoping, pneumatic cylinder that is extended with a compressible bulb. The cylinder engages a pivotal lever that pulls the cable downwardly when the cylinder is extended, thereby applying tension to the harness.

It is therefore an object of the present invention to provide a device that allows a user to conveniently apply traction in the comfort of a home or office.

It is another object of the present invention to provide a traction device that is angularly and length-adjustable.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
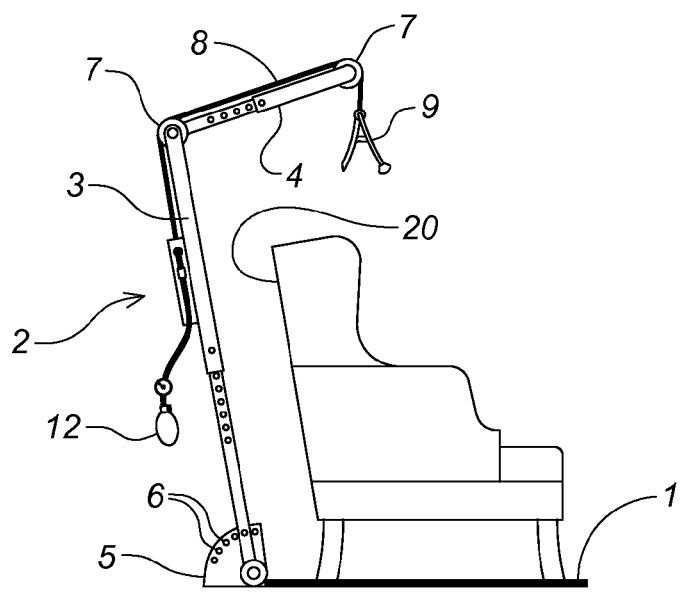
FIG. 1 is a side, plan view of the traction device according to the present invention, properly anchored beneath a chair.
Figure 2:
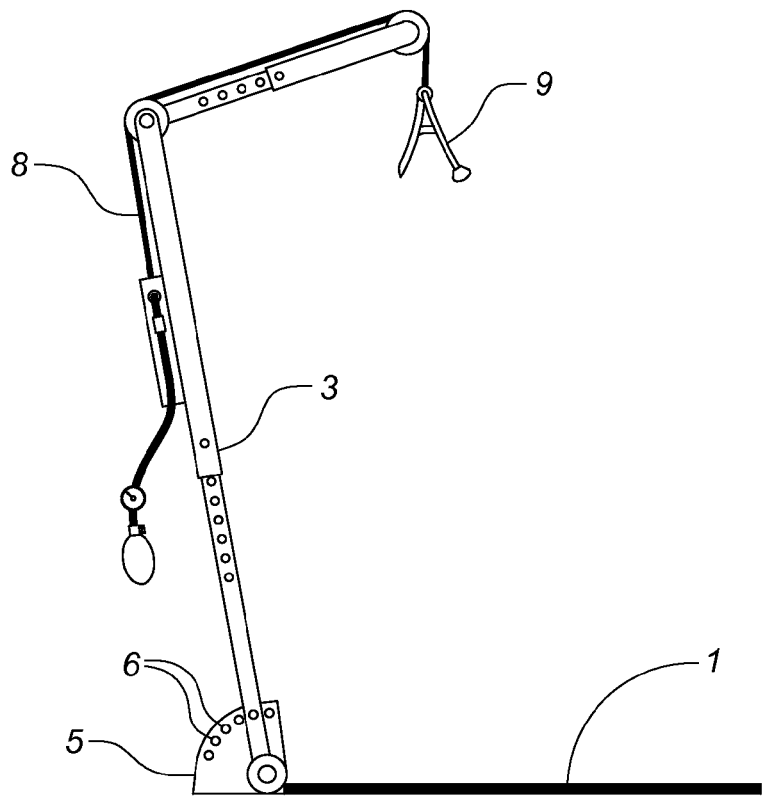
FIG. 2 is an isolated, side view of the traction device.
Figure 3:
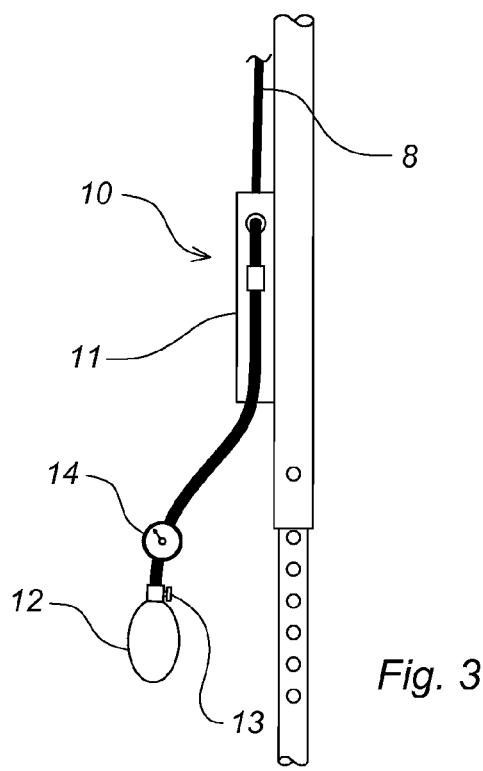
FIG. 3 is an isolated view of the tensioning mechanism housing.
Figure 4:
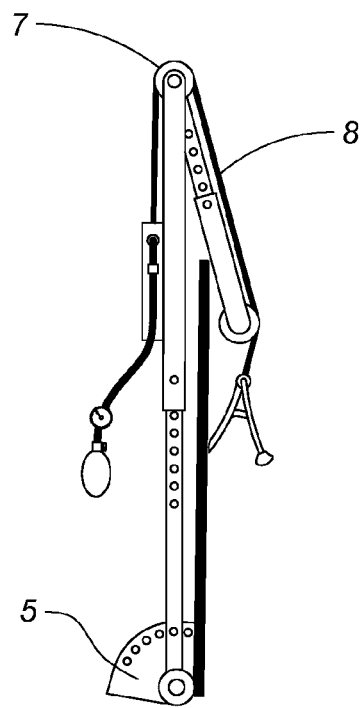
FIG. 4 depicts the device in a collapsed orientation.
Figure 5:
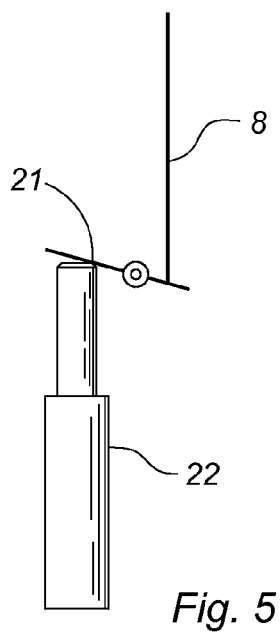
FIG. 5 is an isolated view of the tensioning mechanism.

The present invention relates to a traction device comprising a base panel 1 having a frame member 2 pivotally attached to an edge thereof. The frame member is formed of a telescoping leg 3 with a telescoping, pivotal arm 4 extending from an upper end thereof. Attached to the base panel, and adjacent to the leg, is an adjustment plate 5 having a plurality of radially-disposed apertures 6 thereon, each for selectively aligning with an opening on the leg; a locking pin is inserted into the aligned apertures, allowing the angle of the leg relative to the base panel to be adjusted, as desired. For example, some chairs have oblique backrests 20 whereby a vertical leg would create a traction vector that is not parallel with the spine. Conversely, a user may attain greater relief from a misaligned traction vector for a given ailment or injury.

Both the arm and the leg include a pulley 7 that guides a tensioning cable 8 along the frame member. A neck harness 9 of the type generally known in the art is disposed at a distal end of the cable for securing to a patient's head. A proximal end of the cable extends through a height-adjustable tensioning mechanism 10 mounted on the leg. The tensioning mechanism is formed of a housing 11 having a telescoping, pneumatic cylinder 22 received therein. A compressible bulb 12 allows a user to pressurize the cylinder to a desired level within a predetermined range. The bulb includes a check valve that maintains pressure within the cylinder until air is released by a relief valve 13. When pressurized, the cylinder extends to lift an end of a pivotal lever 21, causing an opposing end to pull the cable downwardly to apply tension to the harness. A pressure gauge 14 allows a user to monitor the relative amount of tension being applied.

To use the traction device, a patient simply slides the base panel beneath a chair or other anchoring device and adjusts the frame height and angle. The tensioning mechanism housing is vertically adjusted on the frame leg so that the harness is applying a minimal amount of force to the neck when the user is seated. The cylinder is extended until the desired amount of tension is applied to the harness.

The above-described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A traction device comprising:
a base panel;
a leg pivotally attached to said base panel;
an arm extending from said leg;
a tensioning cable extending along said leg and said arm, said tensioning cable having a proximal end and a distal end;
a harness at the distal end of said tensioning cable for fastening to a patient's head;
a pivotal lever attached to the proximal end of said tensioning cable;
a telescoping cylinder engaging said pivotal lever;
means for automatically extending and retracting said telescoping cylinder to pivot said lever thereby applying a desired amount of tension to said tensioning cable;
means for angularly adjusting said leg relative to said base panel to vary a biasing direction of said tensioning cable.

2. The traction device according to claim 1 wherein said means for angularly adjusting said leg relative to said base panel comprises:
an adjustment plate attached to said base panel, and adjacent to said leg, said adjustment plate having a plurality of radially-disposed apertures thereon;
an opening on said leg for selectively aligning with one of said apertures;
a locking pin removably inserted within said opening and one of said apertures to fix said leg at a desired angle.

3. The traction device according to claim 1 wherein said means for automatically extending and retracting said telescoping cylinder comprises a compressible bulb in fluid communication with said telescoping cylinder whereby repeatedly compressing said bulb delivers pressurized air to said telescoping cylinder, causing said telescoping cylinder to pivot said lever in a first direction.

4. The traction device according to claim 3 wherein said means for automatically extending and retracting said telescoping cylinder further comprises a relief valve for releasing pressurized air from said telescoping cylinder thereby pivoting said lever in a second direction, opposite to said first direction.

5. A traction device comprising:
a base panel;
a leg pivotally attached to said base panel;
an arm extending from said leg;
a tensioning cable extending along said leg and said arm, said tensioning cable having a proximal end and a distal end;
a harness at the distal end of said tensioning cable for fastening to a patient's head;
a pivotal lever attached to the proximal end of said tensioning cable;
a telescoping cylinder engaging said pivotal lever;
means for automatically extending and retracting said telescoping cylinder to pivot said lever thereby applying a desired amount of tension to said tensioning cable.

* * * * *